(12) United States Patent
Fabo et al.

(10) Patent No.: US 8,439,884 B2
(45) Date of Patent: May 14, 2013

(54) COMPONENT MAKING IT EASIER TO FASTEN A STOMA BANDAGE TO SKIN

(75) Inventors: Tomas Fabo, Molnlycke (SE); Bengt Soderstrom, Molndal (SE); Anna Svensby, Gothenburg (SE)

(73) Assignee: Molnlycke Health Care AB, Gothenburg (SE)

( * ) Notice: Subject to any disclaimer, the term of this patent is extended or adjusted under 35 U.S.C. 154(b) by 838 days.

(21) Appl. No.: 11/794,986

(22) PCT Filed: Jan. 9, 2006

(86) PCT No.: PCT/SE2006/000023
§ 371 (c)(1),
(2), (4) Date: Sep. 11, 2007

(87) PCT Pub. No.: WO2006/075948
PCT Pub. Date: Jul. 20, 2006

(65) Prior Publication Data
US 2008/0009779 A1      Jan. 10, 2008

(30) Foreign Application Priority Data

Jan. 11, 2005 (SE) .................... 0500062-5

(51) Int. Cl.
| | |
|---|---|
| A61F 5/44 | (2006.01) |
| A61F 5/443 | (2006.01) |
| A61F 5/445 | (2006.01) |
| A61L 24/00 | (2006.01) |
| A61B 19/00 | (2006.01) |

(52) U.S. Cl.
USPC ........... 604/338; 604/332; 604/337; 604/339; 604/344; 604/356; 428/446; 428/447

(58) Field of Classification Search .................. 604/332, 604/337, 338, 339, 344, 348, 355, 356; 600/32; 428/446, 447, 145, 147, 149; 528/901
See application file for complete search history.

(56) References Cited

U.S. PATENT DOCUMENTS

| | | |
|---|---|---|
| 1,491,011 A | 4/1924 | Hodgin |
| 3,128,030 A | 4/1964 | Davies |
| 3,630,195 A | 12/1971 | Santomieri |

(Continued)

FOREIGN PATENT DOCUMENTS

| | | |
|---|---|---|
| AU | 2004244939 | 12/2005 |
| AU | 2006205240 | 6/2007 |

(Continued)

OTHER PUBLICATIONS

Online encyclopedia article "Ethylene-vinyl acetate" accessed Apr. 9, 2010. http://en.wikipedia.org/wiki/Ethylene-Vinyl_Acetate.*

(Continued)

*Primary Examiner* — Leslie Deak
*Assistant Examiner* — Adam Marcetich
(74) *Attorney, Agent, or Firm* — Ballard Spahr LLP

(57) ABSTRACT

The present invention relates to a component (1) making it easier to fasten a stoma bandage (6) to skin. According to the invention, the component comprises a plastic film (2) coated with a layer (3) of a soft and skin-compatible silicone elastomer which adheres to skin. The component also has a through-opening (4) intended to be applied around a stoma.

19 Claims, 4 Drawing Sheets

U.S. PATENT DOCUMENTS

| | | | | |
|---|---|---|---|---|
| 4,039,707 | A | * | 8/1977 | O'Malley .................... 428/41.8 |
| 4,219,023 | A | | 8/1980 | Galindo |
| 4,231,369 | A | | 11/1980 | Sorensen et al. |
| 4,336,806 | A | | 6/1982 | Eldridge, Jr. |
| 4,505,976 | A | * | 3/1985 | Doehnert et al. ....... 428/355 CP |
| 4,621,029 | A | | 11/1986 | Kawaguchi |
| 4,775,374 | A | | 10/1988 | Cilento et al. |
| 4,791,149 | A | | 12/1988 | Pocknell |
| 4,925,671 | A | * | 5/1990 | Abber et al. ................. 424/448 |
| 5,074,852 | A | | 12/1991 | Castellana et al. |
| 5,160,330 | A | | 11/1992 | Cross |
| 5,270,358 | A | * | 12/1993 | Asmus ............................ 524/55 |
| 5,545,154 | A | | 8/1996 | Oberholtzer |
| 5,566,031 | A | | 10/1996 | Meyr et al. |
| 5,944,696 | A | | 8/1999 | Bayless et al. |
| 5,951,533 | A | | 9/1999 | Freeman |
| 6,171,594 | B1 | * | 1/2001 | Nielsen ........................ 424/744 |
| 6,284,941 | B1 | * | 9/2001 | Cox et al. ...................... 602/48 |
| 6,387,082 | B1 | | 5/2002 | Freeman |
| 6,471,985 | B2 | | 10/2002 | Guyuron et al. |
| 6,479,724 | B1 | | 11/2002 | Areskoug et al. |
| 6,846,508 | B1 | * | 1/2005 | Colas et al. .................. 427/2.31 |
| 7,192,420 | B2 | | 3/2007 | Whiteford |
| 2004/0102744 | A1 | * | 5/2004 | Fattman ........................ 604/344 |
| 2005/0136266 | A1 | * | 6/2005 | Zhou et al. ................... 428/447 |
| 2006/0228318 | A1 | | 10/2006 | Fabo |

FOREIGN PATENT DOCUMENTS

| | | |
|---|---|---|
| AU | 2006205241 | 6/2007 |
| AU | 2007358685 | 2/2010 |
| CA | 2523234 | 10/2005 |
| CA | 2592774 | 7/2007 |
| CA | 2594402 | 7/2007 |
| CA | 2696957 | 2/2010 |
| CN | 200480016197.2 | 12/2005 |
| CN | 200680001721.8 | 7/2007 |
| CN | 200680002032.9 | 7/2007 |
| EP | 0231508 | 8/1987 |
| EP | 0 300 620 A1 | 1/1989 |
| EP | 1 424 088 A1 | 6/2004 |
| EP | 1557145 A2 | 7/2005 |
| EP | 2004735835 | 10/2005 |
| EP | 2006700065 | 6/2007 |
| EP | 2006700189 | 7/2007 |
| EP | 2007769060 | 3/2010 |
| GB | 1 274 382 | 5/1972 |
| JP | 59036608 A | 2/1984 |
| JP | 2006517019 | 11/2005 |
| JP | 2007550333 | 7/2007 |
| JP | 2007550334 | 7/2007 |
| KR | 1020077018219 | 8/2007 |
| KR | 1020077018221 | 8/2007 |
| KR | 1020107004913 | 3/2010 |
| MX | PA/a/2005/012868 | 11/2005 |
| MX | a/2007/008180 | 7/2007 |
| MX | a/2007/008270 | 7/2007 |
| RU | 2005141426 | 12/2005 |
| RU | 2010112984 | 4/2010 |
| SE | 510907 C2 | 7/1999 |
| SE | 526906 C2 | 11/2005 |
| SE | 05000625 | 7/2006 |
| WO | WO-96/03167 A1 | 2/1996 |
| WO | WO 96/09076 | 3/1996 |
| WO | WO-98/53778 A1 | 12/1998 |
| WO | WO 99/26565 | 6/1999 |
| WO | WO-99/61077 A1 | 12/1999 |
| WO | WO-99/61078 A1 | 12/1999 |
| WO | WO-00/10540 A1 | 3/2000 |
| WO | WO-00/74738 A1 | 12/2000 |
| WO | WO-01/37782 A2 | 5/2001 |
| WO | WO 02/28447 | 4/2002 |
| WO | 03/026541 A1 | 4/2003 |
| WO | WO-03/028601 A2 | 4/2003 |
| WO | WO-03/079919 A1 | 10/2003 |
| WO | WO-2004/108175 A1 | 12/2004 |
| WO | WO-2006/075949 A1 | 7/2006 |
| WO | WO 2008/057155 | 5/2008 |
| ZA | 200509900 | 12/2005 |
| ZA | 2007/05632 | 7/2007 |

OTHER PUBLICATIONS

3M Products website, "Polyethylene Foam Tape 9776" accessed Apr. 9, 2010. http://products3.3m.com/catalog/us/en001/healthcare/medical_specialties/node_D7B59V8CXGbe/root_GST1T4S9TCgv/vroot_GSJ6V2DG18ge/gvel_GSQGG5PDQSgl/theme_us_medicalspecialties_3_0/command_AbcPageHandler/output_html.*

U.S. Appl. No. 10/553,953, filed Jun. 12, 2006, T. Fabo.

U.S. Appl. No. 11/794,942, filed Sep. 18, 2007, T. Fabo.

U.S. Appl. No. 12/671,781, filed Aug. 31, 2010, T. Fabo.

International Search Report with Written Opinion issued on Sep. 14, 2004 for Intl. App. No. PCT/SE2004/000848, filed on Jun. 2, 2000 (Inventor—T. Fabo; Applicant—Molnlycke Health Care AB; pp. 1-5).

International Preliminary Report on Patentability issued on Sep. 30, 2005 for Intl. App. No. PCT/SE2004/000848, filed on Jun. 2, 2000 (Inventor—T. Fabo; Applicant—Molnlycke Health Care AB; pp. 1-7).

Restriction Requirement issued on Sep. 15, 2008 for U.S. Appl. No. 10/553,953, filed Jun. 12, 2006 (Inventor—T. Fabo; Applicant—Molnlycke Health Care AB pp. 1-5).

Response to Restriction Requirement filed on Oct. 15, 2008 for U.S. Appl. No. 10/553,953, filed Jun. 12, 2006 (Inventor—T. Fabo; Applicant—Molnlycke Health Care AB; pp. 1-3).

Non-Final Office Action issued on Dec. 16, 2008 for U.S. Appl. No. 10/553,953, filed Jun. 12, 2006 (Inventor—T. Fabo; Applicant—Molnlycke Health Care AB; pp. 1-13).

Response to Non-Final Office Action filed on Mar. 16, 2009 for U.S. Appl. No. 10/553,953, filed Jun. 12, 2006 (Inventor—T. Fabo; Applicant—Molnlycke Health Care AB; pp. 1-11).

Final Office Action issued on May 19, 2009 for U.S. Appl. No. 10/553,953, filed Jun. 12, 2006 (Inventor—T. Fabo; Applicant—Molnlycke Health Care AB; pp. 1-18).

Appeal Brief filed on Feb. 16, 2010 for U.S. Appl. No. 10/553,953, filed Jun. 12, 2006 (Inventor—T. Fabo; Applicant—Molnlycke Health Care AB; pp. 1-20).

Examiner's Answer to Appeal Brief issued on May 17, 2010 for U.S. Appl. No. 10/553,953, filed Jun. 12, 2006 (Inventor—T. Fabo; Applicant—Molnlycke Health Care AB; pp. 1-24).

RCE/Amendment filed on Jul. 19, 2010 for U.S. Appl. No. 10/553,953, filed Jun. 12, 2006 (Inventor—T. Fabo; Applicant—Molnlycke Health Care AB; pp. 1-13).

International Search Report with Written Opinion issued on Apr. 27, 2006 for Intl. App. No. PCT/SE2006/000024, filed on Jan. 9, 2006 (Inventor—Fabo et al.; Applicant—Molnlycke Health Care AB; pp. 1-6).

International Preliminary Report on Patentability issued Jul. 17, 2007 for Intl. App. No. PCT/SE2006/000024, filed on Jan. 9, 2006 (Inventor—Fabo et al.; Applicant—Molnlycke Health Care AB; pp. 1-5).

Non Final Office Action issued on Nov. 4, 2008 for U.S. Appl. No. 11/794,942, filed Sep. 18, 2007 (Inventor—T. Fabo et al.; Applicant—Molnlycke Health Care AB; pp. 1-9).

Response to Office Action filed on Feb. 4, 2009 for U.S. Appl. No. 11/794,942, filed Sep. 18, 2007 (Inventor—T. Fabo et al.; Applicant—Molnlycke Health Care AB; pp. 1-16).

Final Office Action issued on Apr. 29, 2009 for U.S. Appl. No. 11/794,942, filed Sep. 18, 2007 (Inventor—T. Fabo et al.; Applicant—Molnlycke Health Care AB; pp. 1-10).

RCE/Amendment filed on Jul. 29, 2009 for U.S. Appl. No. 11/794,942, filed Sep. 18, 2007 (Inventor—T. Fabo et al.; Applicant—Molnlycke Health Care AB; pp. 1-11).

Non-Final Office Action issued on Sep. 17, 2009 for U.S. Appl. No. 11/794,942, filed Sep. 18, 2007 (Inventor—T. Fabo et al.; Applicant—Molnlycke Health Care AB; pp. 1-8).

Response to Office Action filed on Dec. 17, 2009 for U.S. Appl. No. 11/794,942, filed Sep. 18, 2007 (Inventor—T. Fabo et al.; Applicant—Molnlycke Health Care AB; pp. 1-11).

Final Office Action issued on Feb. 25, 2010 for U.S. Appl. No. 11/794,942, filed Sep. 18, 2007 (Inventor—T. Fabo et al.; Applicant—Molnlycke Health Care AB; pp. 1-10).

Amendment after Final filed on Jun. 25, 2010 for U.S. Appl. No. 11/794,942, filed Sep. 18, 2007 (Inventor—T. Fabo et al.; Applicant—Molnlycke Health Care AB; pp. 1-13).

Advisory Action issued on Jul. 29, 2010 for U.S. Appl. No. 11/794,942, filed Sep. 18, 2007 (Inventor—T. Fabo et al.; Applicant—Molnlycke Health Care AB; pp. 1-9).

Appeal Brief filed on Nov. 19, 2010 for U.S. Appl. No. 11/794,942, filed Sep. 18, 2007 (Inventor—T. Fabo et al.; Applicant—Molnlycke Health Care AB; pp. 1-15).

Examiner's Answer to Appeal Brief issued on Jan. 20, 2011 for U.S. Appl. No. 11/794,942, filed Sep. 18, 2007 (Inventor—T. Fabo et al.; Applicant—Molnlycke Health Care AB; pp. 1-10).

Reply Brief filed on Mar. 18, 2010 for U.S. Appl. No. 11/794,942, filed Sep. 18, 2007 (Inventor—T. Fabo et al.; Applicant—Molnlycke Health Care AB; pp. 1-2).

International Search Report with Written Opinion issued on May 13, 2008 for Intl. App. No. PCT/SE2007/050514, filed on Sep. 6, 2007 (Inventor—Svensby et al.; Applicant—Molnlycke Health Care AB; pp. 1-10).

International Preliminary Report on Patentability issued on Mar. 9, 2010 for Intl. App. No. PCT/SE2007/050514, filed on Sep. 6, 2007 (Inventor—Svensby et al.; Applicant—Molnlycke Health Care AB; pp. 1-6).

Non-Final Office Action issued on Jan. 17, 2012 for U.S. Appl. No. 12/671,781, filed Aug. 31, 2010 (Inventor—Svensby et al.; Applicant—Molnlycke Health Care AB; pp. 1-7).

Response to Office Action filed on May 7, 2012 for U.S. Appl. No. 12/671,781, filed Aug. 31, 2010 (Inventor—Svensby et al.; Applicant—Molnlycke Health Care AB; pp. 1-12).

International Search Report with Written Opinion issued on Apr. 27, 2006 for Intl. App. No. PCT/SE2006/000023, filed on Jan. 9, 2006 (Inventor—Fabo et al.; Applicant—Molnlycke Health Care AB; pp. 1-6).

International Preliminary Report on Patentability issued Jul. 17, 2007 for Intl. App. No. PCT/SE2006/000023, filed on Jan. 9, 2006 (Inventor—Fabo et al.; Applicant—Molnlycke Health Care AB; pp. 1-5).

Office Action issued on May 27, 2010 for CN 200680001721.8, national phase of Intl. App. No. PCT/SE2006/000024, filed on Jan. 9, 2006 (Inventor—Fabo et al.; Applicant—Molnlycke Health Care AB; pp. 1-6).

Office Action issued on Aug. 31, 2010 for JP 2007-550334, national phase of Intl. App. No. PCT/SE2006/000024, filed on Jan. 9, 2006 (Inventor—Fabo et al.; Applicant—Molnlycke Health Care AB; pp. 1-2).

Office Action issued on Nov. 24, 2008 in SE Pat. App. 0500063-3, corresponding application of Intl. App. No. PCT/SE2006/000024, filed on Jan. 9, 2006 (Inventor—Fabo et al.; Applicant—Molnlycke Health Care AB; pp. 1-6).

Extended European Search Report issued May 6, 2010 for European Patent Application No. 06700189, filed on Sep. 1, 2006 (Inventor—Tomas Fabo; Applicant—Mölnlycke Health Care AB; pp. 1-7).

Request for Continued Examination and Response to Final Office Action filed on Dec. 6, 2012 for U.S. Appl. No. 12/671,781, filed Aug. 31, 2010 (Inventor—Svensby et al.; Applicant—Molnlycke Health Care AB; pp. 1-21).

Applicant Initiated Interview Summary issued Nov. 28, 2012 for U.S. Appl. No. 12/671,781, filed Aug. 31, 2010 (Inventor—Svensby et al.; Applicant—Molnlycke Health Care AB; pp. 1-4.

Applicant Initiated Interview Summary issued Nov. 8, 2012 for U.S. Appl. No. 12/671,781, filed Aug. 31, 2010 (Inventor—Svensby et al.; Applicant—Molnlycke Health Care AB; pp. 1-5.

Final Office Action issued Aug. 6, 2012 for U.S. Appl. No. 12/671,781, filed Aug. 31, 2010 (Inventor—Svensby et al.; Applicant—Molnlycke Health Care AB; pp. 1-18.

* cited by examiner

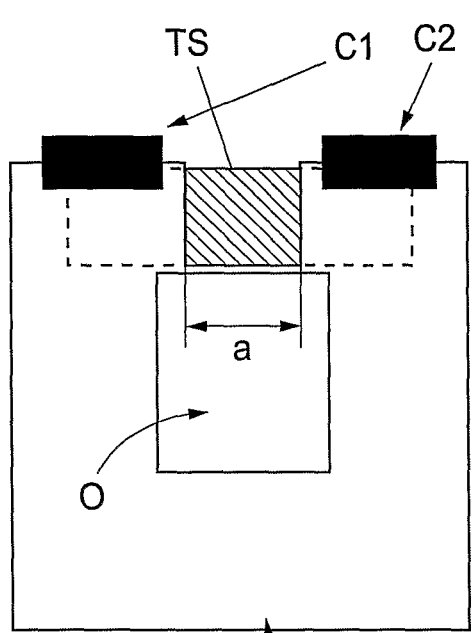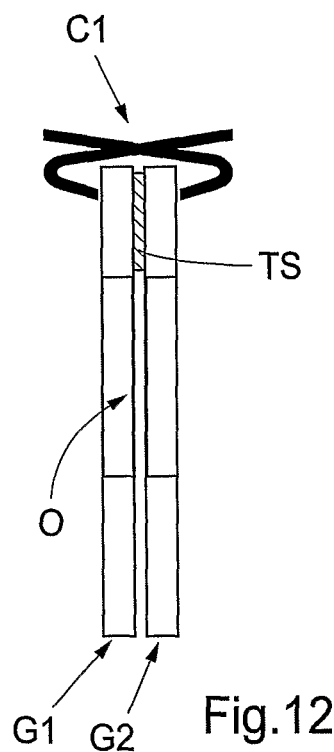
Fig. 11    Fig. 12
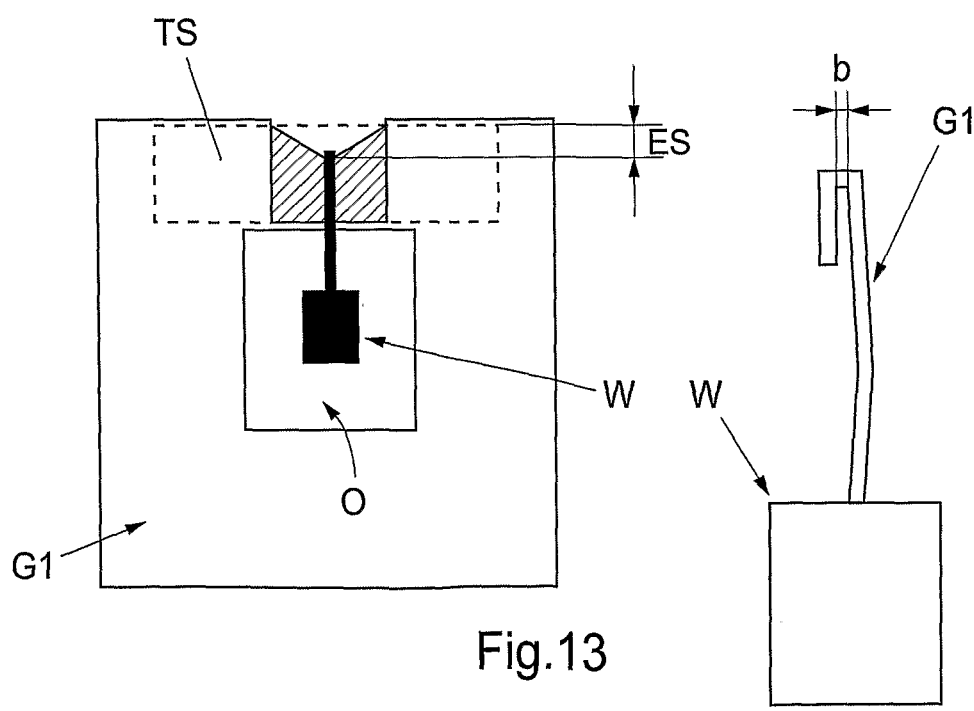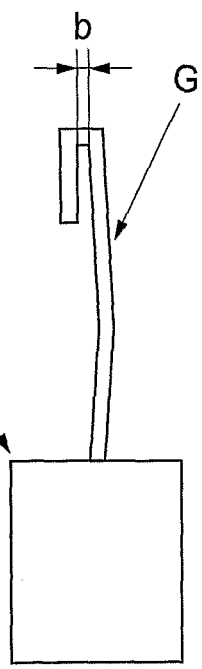
Fig. 13    Fig. 14

COMPONENT MAKING IT EASIER TO FASTEN A STOMA BANDAGE TO SKIN

TECHNICAL FIELD

The present invention relates to a component making it easier to fasten a stoma bandage to skin.

BACKGROUND TO THE INVENTION

Since the end of the 1970s, hydrocolloid-based adhesives have been used in systems for fastening stoma bags to patients who have undergone an ostomy procedure. Such systems function well in many cases, but it is not uncommon for skin irritation or skin damage to occur in the area around the stoma.

The present invention aims to provide a component which improves systems for fastening stoma bags and which eliminates or at least to a large extent reduces the risk of skin irritation or skin damage occurring in the area around the stoma of a patient who has undergone an ostomy procedure.

DISCLOSURE OF THE INVENTION

According to the invention, these aims are achieved by a component making it easier to fasten a stoma bandage to skin, characterized in that it comprises a plastic film coated with a layer of a soft and skin-compatible silicone elastomer which adheres to skin, and in that it has a through-opening intended to be applied around a stoma. Since the silicone elastomer is very soft, it can penetrate down into all irregularities in the skin so that fluid, which leaks from the stoma, cannot spread out across the skin, and this means it is easier to ensure leaktightness than is the case with the plates of hydrocolloid material that are presently used in fastening systems for stoma bags. The component according to the invention is also much softer and shapeable than plates of hydrocolloid material, which means that the edge of the opening in the component can be applied very close to the stoma without risk of chafing, which causes irritation or bleeding of the mucous membrane at the base of the stoma. The component according to the invention maintains its integrity upon contact with fluid, unlike hydrocolloid material which tends to disintegrate upon contact with fluid, and this means that the opening in the hydrocolloid material tends to increase in size over time, which in turn means that an ever greater area of the skin around the stoma may become exposed to material leaking from the intestine, with corrosion damage as a consequence. The component according to the invention can also be stretched together with the skin so that there is considerably less risk of shearing between skin and adhesive, which shearing can give rise to mechanical damage to the skin. A further advantage of the component according to the invention is that it can be reapplied after removal from the skin because it does not to any appreciable extent pull off skin cells with it during removal, which would otherwise reduce the adherence surface available for reapplication. Hydrocolloid material, when removed, pulls off so many skin cells that its surface area available for reapplication is considerably decreased after removal. Components according to the invention do not pull off hairs either, and there is therefore no risk of inflammation in the hair follicles resulting from use of such components. Therefore, skin irritation as a consequence of shaving can also be avoided using components according to the invention. In contrast to hydrocolloid plates, components according to the invention can also be made transparent, which means that it is easier to apply the components in the correct place than if they were non-transparent, and easier to monitor the state of the skin without having to detach the component.

In a preferred embodiment, the adherence of the silicone elastomer to dry skin is 0.4-3 N/25 mm, and the weight per unit area of the layer of silicone elastomer is greater than 30 $g/m^2$, preferably greater than 70 $g/m^2$. Moreover, the silicone elastomer has a softness of 8-22 mm, preferably 12-17 mm. The adhesives used on standard stoma bandages, for example on hydrocolloid-based stoma bandages, have a softness of 2-5 mm. The plastic film has a thickness of less than 100 micrometers, preferably less than 40 micrometers, and it particularly preferably has a thickness of 15-40 micrometers. Moreover, the edge softness of the plastic film is greater than 2 mm, preferably greater than 4 mm, and the edge softness of the component is greater than 2 mm, preferably greater than 3 mm. The stretchability of component 1 should preferably be such that the force needed to stretch or elongate the component 5% is less than 1.5 N and preferably less than 1 N.

One or more skin-care substances can also be mixed into the hydrophobic silicone elastomer. These substances can be hydrophilic or hydrophobic and can also be formulated to give the component better mechanical or physical properties.

A release layer which is removed prior to use of the component is preferably applied to the silicone elastomer on the side opposite from the plastic film.

The component can also be integrated in a stoma bandage.

BRIEF DESCRIPTION OF THE DRAWINGS

The invention will now be described with reference to the attached figures where:

FIGS. 11-14 illustrate a method for measuring edge softness.

DESCRIPTION OF EMBODIMENTS

Figure 1:
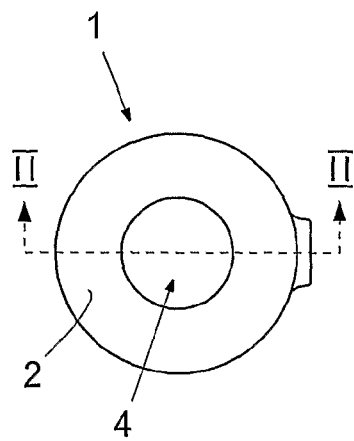
FIG. 1 shows a schematic plan view of a component according to a first preferred embodiment of the invention.
Figure 2:
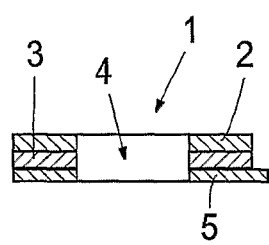
FIG. 2 shows a cross section along the line II-II in FIG. 1.

FIGS. 1 and 2 show a first embodiment of a component 1 included in a fastening system for a stoma bandage. In the embodiment shown, the component 1 is circular and comprises a plastic film 2, preferably of polyurethane plastic, coated with an adhesive layer 3 of a soft and skin-compatible silicone elastomer which adheres to skin. The thickness of the plastic film is between 20 and 30 micrometers, and the weight per unit area of the adhesive layer is equal to or greater than 30 $g/m^2$. The component 1 also has a through-opening 4. Before use, the adhesive layer 3 is protected by a release layer 5 which can comprise a polyethylene film or a polyethylene-coated paper. To make detachment of the release layer 5 easier when it is to be removed before application of the component 1, it has a part which extends laterally outside the component 1.

A major problem of hydrocolloid plates for fastening stoma bags is that they are stiff and can cause chafing along the edges, both against the skin around the stoma and also against the protruding part of the intestine. It is desirable for the component consisting of film 2 and adhesive 3 to have a high degree of softness at least in the inner and outer edges of the plate in order to avoid chafing against skin and intestine.

By using the very soft silicone elastomer 3 in combination with a thin and easily stretchable plastic film 2 as support, the component consisting of plastic film and silicone elastomer is afforded a very high degree of edge softness, even up to a component thickness of over 1 mm.

The edge softness is determined by the method described below.

A test specimen TS measuring 25×100 mm is clamped between two identical Plexiglas discs G1, G2, as is illustrated in FIGS. 11-13. The test specimen TS must be fully stretched, but without tensile stresses in any direction. The Plexiglas discs G1, G2 have a central opening O which extends upwards to the top edges of the Plexiglas discs such that the test specimen TS extends in the recess parallel to the top edges of the Plexiglas discs and at right angles to the edges of the recess within the area for the test specimen. The length a of the test specimen in the recess is 20 mm.

A weight W of 10.3 g is then hung over the top edge of the test specimen TS midway between the edges of the recess, as is illustrated in FIG. 13. The weight W is shown in FIG. 14 and comprises a steel wire with a diameter of 1 mm which ends in a loop with a width b=2 mm. After 30 seconds, the number of mm that the edge of the test specimen has dropped under the load is read off. The extent of the deformation, i.e. the position of the lowest point of the deformed edge, is expediently measured by the test specimen being photographed together with a calibrated measurement scale. The number of millimeters ES that the test specimen has dropped after 30 seconds represents a measure of the edge softness. The edge softness ES will be greater than 2 mm in a component according to the present invention.

It is important that the test specimen is held securely in place between the Plexiglas discs during testing, so that those parts of the test specimen's top edge which are located between the Plexiglas discs cannot be displaced downward during the test. For this purpose, FIGS. 11 and 12 show two clips C1 and C2 which prevent movement of those parts of the test specimen located between the Plexiglas discs. Such securing can of course be achieved using other types of clamping means or in some other fashion, for example by quite simply gluing the test specimen in the Plexiglas discs, as is indicated in FIG. 13 by the absence of the clips C1 and C2.

The method described above is also used to determine the edge softness of the plastic film on its own.

To achieve the necessary edge softness, the support, i.e. the plastic film 2, must be thin and pliable and have a very high degree of edge softness measured by the method described above, so as not to chafe or cut into the mucous membrane at the stoma base. The edge softness of the film should be greater than 2 mm, preferably greater than 4 mm. Examples of good support materials are polyurethane films with a thickness of less than 100 micrometers, preferably less than 40 micrometers. The thickness of the film should most preferably be 10-40 micrometers.

The adhesive layer 3 is made up of an addition-curing RTV (room temperature vulcanizing) silicone system which, after admixture, crosslinks and forms a self-adhesive elastomer.

Examples of RTV addition-curing silicone systems are given in EP 0 300 620 A1 which describes what it calls "gel-forming compositions" comprising an alkenyl-substituted polydiorganosiloxane, an organosiloxane containing hydrogen atoms bound to some of the silicone atoms, and a platinum catalyst.

An example of a commercially available RTV silicone system is Wacker SilGel 612 from Wacker-Chemie GmbH, Munich, Germany. This is a two-component system. By varying the proportions between the two components A:B from 1.0:0.7 to 1.0:1.3, it is possible to vary the softness and level of adherence of the elastomer that is formed.

Examples of other soft silicone elastomers which adhere to dry skin are NuSil MED-6340, NuSil MED3-6300, NuSil MED12-6300 from NuSil Technology, Carpinteria, Ga., USA, and Dow Corning 7-9800 from Dow Corning Corporation, Midland, USA.

The silicone elastomer layer 3 can also comprise a number of additives for different purposes, for example paraffin or ZnO for controlling the rheology, urea for reducing the drying-out of the skin, anti-inflammatory preparations such as hydrocortisone, antimicrobial preparations, buffering additives for lowering the pH value of pH-neutral water to 3.5-6.0, preferably to 4.5-5.8 and particularly preferably to 4.9-5.5. Such pH-buffering additives are described in WO 02/28447 A1, to which document reference may be made for further details.

Figure 3:
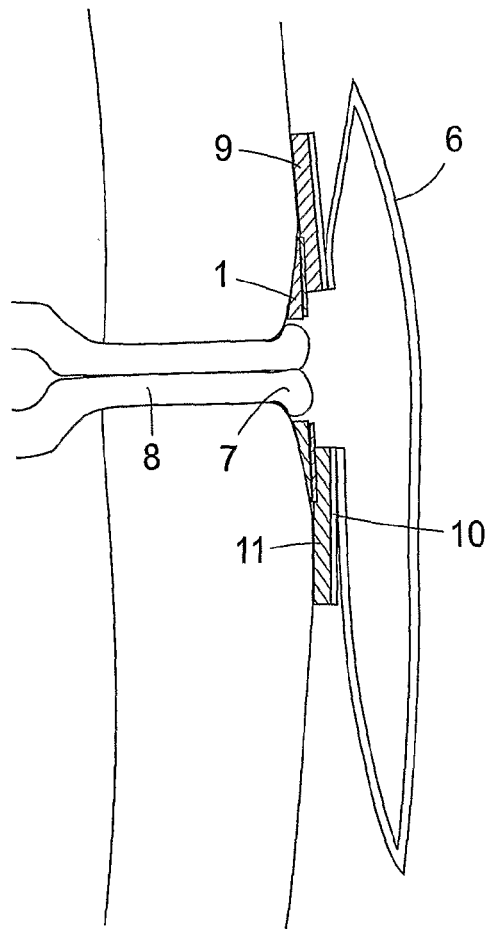
FIG. 3 shows a schematic view of a fastening system for a stoma bandage in which a component according to FIG. 1 is included.

FIG. 3 shows a use of the component 1 in a system for fastening a stoma bandage 6 of conventional construction around a patient's stoma 7. A stoma is that part 7 of an ostomy patient's intestine 8 extending outside the patient's body, as is shown schematically in FIG. 3. The stoma bandage 6 comprises a bag part with an opening, and a fastening part 9 secured to the bag part around this opening. The fastening part 9 comprises a plastic layer 10 coated with an adhesive layer 11 of a hydrocolloid. A component 1 according to the invention is also fitted close to the stoma, and its layer 3 of silicone elastomer is secured to the skin around the stoma 7. The adhesive layer 11 of the fastening part 9 of the stoma bag 6 is secured to the plastic layer 2 of the component 1 in the area nearest to the stoma and is secured to the patient's skin in the area outside the component 1.

Since the silicone elastomer is very soft and has low surface energy, it wets very well to the skin, i.e. it spreads out in the irregularities of the skin and creates a large contact surface between skin and silicone elastomer. This large contact surface helps the silicone elastomer fasten effectively to the skin despite the fact that the silicone elastomer's binding force to skin is not inherently great. The adherence force represents a measure of the energy that is needed to separate/pull off the adhesive layer from skin. A contributory factor explaining why considerable energy and thus a considerable pulling-off force is needed to remove silicone elastomer from the skin, despite the relatively weak binding force, is that a great deal of energy is expended in stretching the soft silicone elastomer before it detaches from the skin. The softer and thicker the layers of silicone elastomer, the more force/energy is needed for removing the elastomer from the skin.

If a harder adhesive is used, a stronger binding force is needed to ensure that the pulling-off force will be as great as for a softer adhesive. A strong binding force between skin and adhesive easily leads to skin cells being pulled away from the skin when the adhesive is being removed.

Another disadvantage of harder adhesives is that these may spread outwards over the course of time and thus increase the contact surface with the skin, which has the result that the pulling-off force increases with time, which can mean that these adhesives eventually become difficult to remove from the skin. In contrast to harder adhesives such as hydrocolloids, softer adhesives such as silicone elastomers achieve their full force of adherence all at once so that their pulling-off force remains constant over time.

Since the silicone elastomer in the layer 3 of the component 1 is very soft, it can penetrate, as has already been mentioned, down into all the irregularities in the skin, so that fluid which escapes from the stoma opening cannot spread out across the skin. The plates of hydrocolloid material 11 which are presently used in fastening systems for stoma bags are stiffer than the component 1. This means that it is more difficult to ensure leaktightness with hydrocolloid plates than it is with a plate configured as the component 1 according to the invention. The risk of irritation or bleeding of the mucous membrane at the base of the stoma 7 is also reduced by virtue of the component 1 according to the invention being soft. The component according to the invention is also more shapeable than plates of hydrocolloid material, which means that the edge of the opening of the component can be easily adapted to the shape of the stoma and can thus be applied very close to the stoma. The stretching of the silicone elastomer and its change of shape during use is predominantly elastic, in contrast to the hydrocolloid adhesive of hydrocolloid-based stoma bandages which constitutes a viscous composition. The component according to the invention is also basically hydrophobic and maintains its integrity upon contact with fluid, in contrast to hydrophobic material which tends to disintegrate upon contact with fluid, with the result that the opening in the hydrocolloid material tends to increase in size over the course of time, which in turn means than an ever greater area of the skin around the stoma may become exposed to material leaking from the intestine, with corrosion damage as a consequence. In this context it should be noted that if the opening of the component 1 is too small, it can be made larger by punching or cutting in order to adapt its size to the stoma. Conventional fastening arrangements for stoma bags are often provided with cutting marks, for example in the form of helical lines, to make this kind of adaptation easier. Such adaptation of size is important for ensuring that the smallest possible area of skin around the stoma comes into contact with the intestinal content collected in the stoma bandage. As has already been mentioned, the shapeability of the component 1 means it is easy to finely adjust the shape of the opening 4 so that this coincides with the cross-sectional shape of the stoma 7, which may deviate from a circular shape.

Moreover, the component 1 according to the invention can be stretched together with the skin, such that there is a significantly reduced risk of shearing between skin and adhesive, which shearing may give rise to mechanical damage of the skin. The stretchability of component 1 should preferably be such that the force needed to stretch or elongate component 1 5% is less than 1.5 N and preferably less than 1 N. The stretchability of component 1 should be measured according to ASTM D 882-02 under the following conditions: width of sample=25 mm; gauge length=100 mm; cross head speed=50 mm/min; reading of the force=at 5% elongation of the sample.

A further advantage of the component according to the invention is that it can be reapplied after removal from the skin because it does not to any appreciable extent pull off skin cells with it when removed. Hydrocolloid material, when removed, pulls off so many skin cells that its adherence to skin decreases considerably after removal. The component 1 according to the invention does not pull off any hairs either, and the use of such components does not therefore pose any risk of inflammation in the hair follicles. Irritation of the skin as a consequence of repeated shaving of the area nearest the stoma can thus also be avoided when using components according to the invention. Components according to the invention can also be made transparent, which means that it is possible to monitor the state of the skin without having to detach the component.

Figure 8:
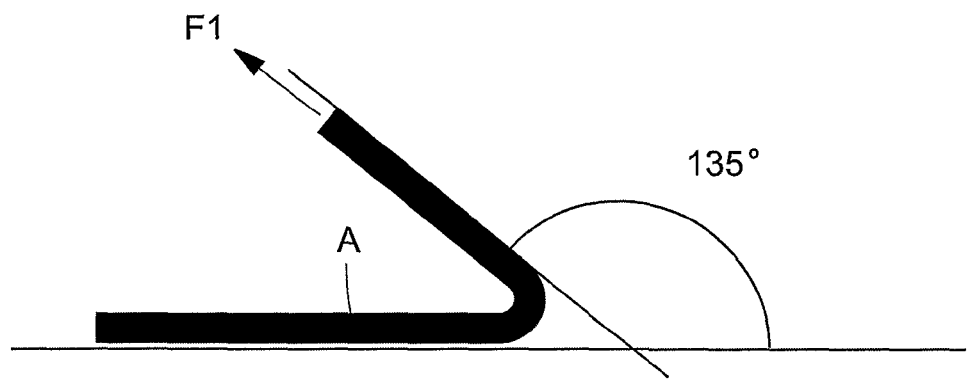
FIG. 8 illustrates measurement of the force of adherence to skin.

Since the properties of the skin vary from person to person, the ability of the adhesive coating 3 to adhere to skin of course also varies for different patients. The force of adherence is also dependent on the thickness of the silicone elastomer and the mechanical properties of the support film. The standard methods for measuring adherence which are employed at the present time make use of plates of various types, for example of steel or glass, and do not give values relevant for measuring adherence to skin. The skin adherence values of an adhesive which are specified below will therefore be measured by a method which is illustrated in FIG. 8 and which has been developed by the Applicant. Strips A of a support material, a polyurethane film with thickness 25±5 micrometers, coated with the adhesive whose force is to be measured, and with a width of 25 mm, are placed on the skin of the back of at least ten healthy subjects of different age and sex and are allowed to remain on the skin for two minutes. The weight per unit area of the adhesive layer will be 100 g/m². The strips A are thereafter removed at a speed of 25 mm/sec and the pulling-off force F1 is measured. The pulling-off angle, that is to say the obtuse angle formed between the skin surface and the pulled-off part of the strip, will be 135°. The measured skin adherence force of the adhesive is represented by the mean value of the measured force F1. Adhesives that can be used in components according to the invention will have an adherence force according to this method of 0.4 N/25 mm. The adherence force is preferably 1-3 N/25 mm.

Figure 9:
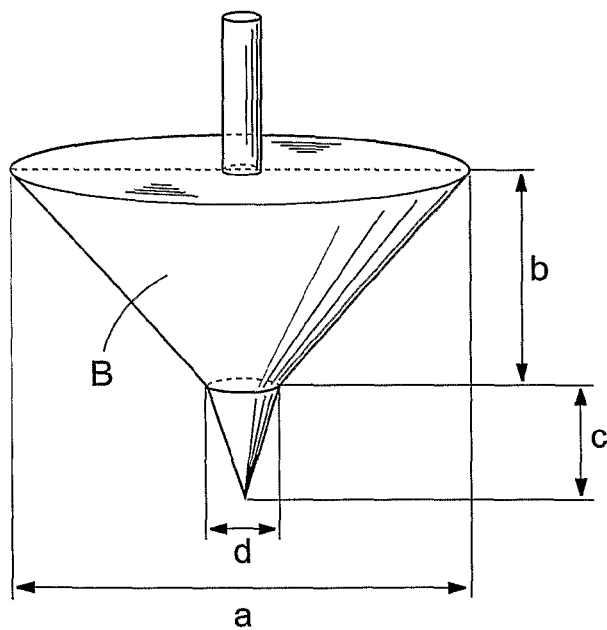
FIG. 9 shows a cone used for measuring softness.
Figure 10:
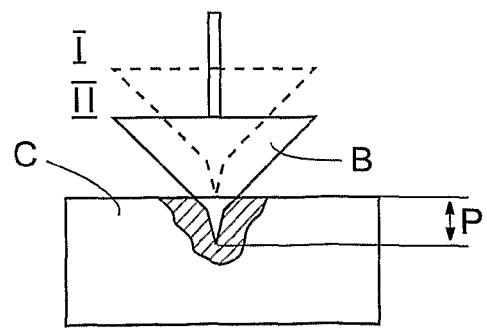
FIG. 10 illustrates a method for measuring softness.

The adhesive according to the invention will have a softness exceeding 8 mm measured by a method based on ASTM D 937 and ASTM D 51580. Certain modifications, which are set out below, have been made to the method. FIGS. 9 and 10 illustrate this modified method of measuring softness of an adhesive by allowing a cone B with a weight of 62.5 g to penetrate by gravity into a 30-mm thick test specimen C of the adhesive whose softness is to be determined. The test specimen is obtained by a cylindrical glass container with internal diameter 60 mm and an inner height of 35-40 mm being filled with adhesive up to a height of 30 mm. For a silicone elastomer, non-cured silicone prepolymer is introduced into the container and is then crosslinked to an elastomer in the glass cylinder. The cone used is shown in FIG. 9 and has the following dimensions: a=65 mm, b=30 mm, c=15 mm and d=8.5 mm. When carrying out the method for measuring softness, the cone B is first lowered to a position I which is shown by broken lines in FIG. 10 and in which the tip of the cone just touches the surface of the test specimen C. The cone B is then released so that it is allowed to penetrate by force of gravity down into the test specimen C. The number of mm the tip of the cone B has penetrated into the test specimen C after 5 seconds is measured and represents the penetration value P, which is higher the softer the test specimen. The penetration value P represents the measure of softness used in the present invention. When carrying out the method, a Penetrometer PNR 10 from Sommer & Runge K G, Germany was used. The softness of the silicone elastomer adhesives used in the component 1 is preferably 8-22 mm, especially preferably 12-17 mm.

By using a soft and skin-compatible adhesive, the risk of fluid from the stoma opening running under the adhesive layer in irregularities of the skin is eliminated or at least significantly reduced if the weight per unit area of the adhesive is sufficiently high. The weight per unit area of the layer 3 of silicone elastomer is preferably greater than 70 g/m². In normal circumstances, the greater the folds and irregularities around a stoma the greater the weight per unit area needed to achieve leaktightness. In some cases, several hundred g/m² may be justified, even up to as much as 2000 g/m².

In addition to increasing the leaktightness, a high weight per unit area and a high degree of softness of the adhesive coating afford a reduced risk of blisters, pustules or other damage occurring on the skin at the edges of the applied adhesive. Such damage can result from movements of the patient which lead to relative movement between skin and adhesive coating or can be caused by the component 1 being exposed to forces from outside, for example the weight of a full stoma bandage. It has been shown that the risk of such damage occurring decreases with a higher weight per unit area and a higher degree of softness of the adhesive coating. This is probably due to the fact that some of the load is taken up by the adhesive layer through deformation and is therefore not transmitted to the skin.

To ensure that only a low application force is needed for applying the component 1 according to the present invention, the softness of the soft and skin-compatible adhesive used is preferably greater than 12 mm. The softer an adhesive, the more rapidly it spreads into any irregularities in the skin, which means that the component 1 according to the invention is leakproof directly after application. A soft adhesive can also take up a greater amount of energy than a harder adhesive before it comes loose under loading, and this reduces the risk of its coming loose when loaded.

Another important property of the component 1 according to the invention is that the skin adherence force of the soft, skin-compatible adhesives used does not change with time, or changes only to a small extent with time, during the period the component is fastened to the skin.

The component 1 is also sterilizable, which means that it can be delivered in sterile packaging if so desired.

Figure 4:
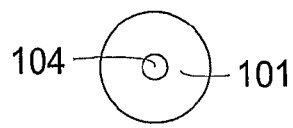
FIGS. 4, 5 and 6 show plan views of a component according to other preferred embodiments of the invention.
Figure 5:
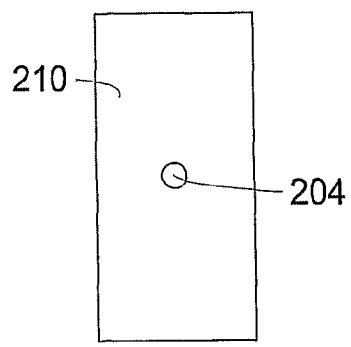
Figure 6:
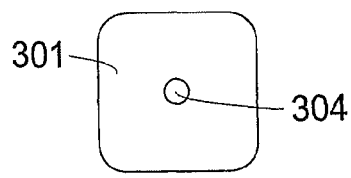
Figure 7:
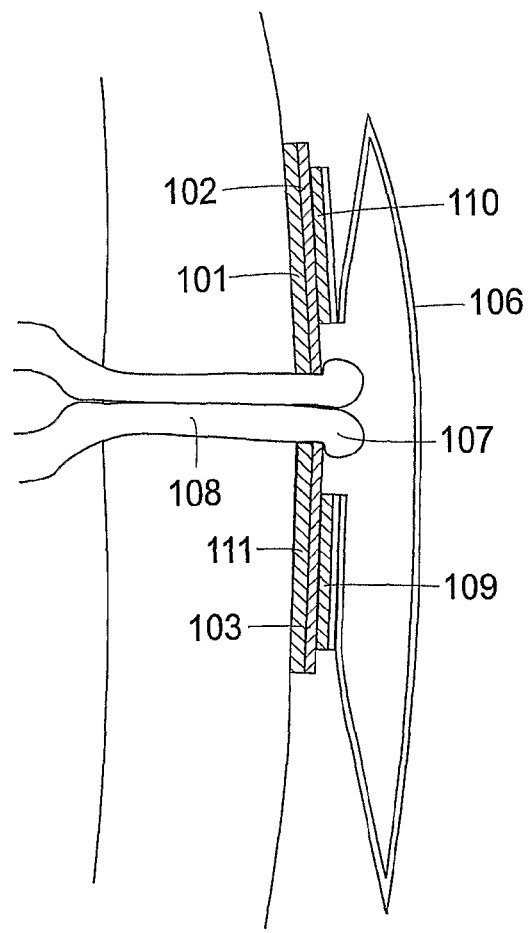
FIG. 7 shows a schematic view of a fastening system for a stoma bandage, in which a component according to one of FIGS. 4-6 is included.

FIGS. 4-6 show other preferred embodiments of components 101, 201 and 301 according to the invention. These components have a similar structure to the component 1 described with reference to FIGS. 1-3 but differ from this in terms of size and, for the components 201 and 301, also in terms of shape. The openings 104, 204 and 304 have the same dimension as the opening 4 in the component 1 in FIGS. 1-3. The components 101, 201 and 301 are of such a size that the whole plate of hydrocolloid material of a conventional stoma bandage can be fastened to the top surface, i.e. to the plastic layer, of the component according to the invention, as is illustrated in FIG. 7 where the plate 109 of a conventional stoma bandage 106 is fastened with its hydrocolloid layer 111 to the plastic layer 102 of a component 101 according to the invention. An advantage of fastening to the component 101 is that the hydrocolloid layer 111 forms a good seal against the plane plastic layer 102 of the component 101. A further advantage is that any fluid between hydrocolloid layer 111 and plastic layer 102 has to flow a substantial distance to reach surrounding skin, which further reduces the risk of fluid leaking out onto the skin from the stoma bandage in FIG. 7.

In an embodiment not shown here, a component according to the embodiments 101, 201 or 301 can form part of a stoma bandage 106 instead of the fastening arrangement 109 shown in FIG. 7.

The described embodiments can of course be modified without departing from the scope of the invention. For example, plastics other than polyurethane can be used for the plastic layer in the component according to the invention. If the component comprises thin plastic layers, it may be expedient to arrange a support layer, for example of polyethylene, on top of the plastic layer in order to make application easier, which support layer is removed after application. The invention is therefore not limited by the content of the attached patent claims.

The invention claimed is:

1. A component making it easier to fasten a stoma bandage to skin, comprising:
    a plastic film coated with a layer of a soft and skin-compatible silicone elastomer which is adapted to adhere to skin, the plastic film having a thickness that is less than 100 micrometers; and
    a through-opening intended to be applied around a stoma, wherein an edge softness of the plastic film is greater than 2 mm and the elastomer has a softness exceeding 8 mm.
2. The component according to claim 1, wherein an adherence of the silicone elastomer to dry skin is 0.4-3 N/25 mm.
3. The component according to claim 2, wherein the edge softness of the plastic film is greater than 4 mm.
4. The component according to claim 2, wherein a weight per unit area of the layer of silicone elastomer is greater than 30 g/m².
5. The component according to claim 2, wherein the silicone elastomer has a softness of 8-22 mm.
6. The component according to claim 2, wherein the edge softness of the component is greater than 2 mm.
7. The component according to claim 2, wherein a stretchability of said component is such that the force needed to stretch the component 5% is less than 1.5 N.
8. The component according to claim 2, wherein a skin care substance is mixed into the silicone elastomer.
9. The component according to claim 2, wherein a release layer which is removed prior to use of the component is applied to the silicone elastomer on the side opposite from the plastic film.
10. The component according to claim 1, wherein the edge softness of the plastic film is greater than 4 mm.
11. The component according to claim 1, wherein a weight per unit area of the layer of silicone elastomer is greater than 30 g/m².
12. The component according to claim 1, wherein the silicone elastomer has a softness of 8-22 mm.
13. The component according to claim 1, wherein the edge softness of the component is greater than 2 mm.
14. The component according to claim 1, wherein a stretchability of said component is such that the force needed to stretch the component 5% is less than 1.5 N.
15. The component according to claim 1, wherein a skin care substance is mixed into the silicone elastomer.
16. The component according to claim 1, wherein a release layer which is removed prior to use of the component is applied to the silicone elastomer on the side opposite from the plastic film.
17. The component according to claim 1, wherein the component is integrated in a stoma bandage.
18. The component according to claim 1, wherein an adherence of the silicone elastomer to dry skin is 1-2.5 N/25 mm, a thickness of the plastic film is 15-40 micrometers, a weight per unit area of the layer of silicone elastomer is greater than 70 g/m², the silicone elastomer has a softness of 12-17 mm, and a stretchability of said component is such that the force needed to stretch the component 5% is less than 1 N.
19. The component of claim 1, wherein the stoma bandage comprises a bag and a fastening part.

* * * * *

UNITED STATES PATENT AND TRADEMARK OFFICE
CERTIFICATE OF CORRECTION

PATENT NO.       : 8,439,884 B2  
APPLICATION NO. : 11/794986  
DATED            : May 14, 2013  
INVENTOR(S)      : Fabo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this
Eighth Day of September, 2015

Michelle K. Lee
*Director of the United States Patent and Trademark Office*